United States Patent [19]

Inaba

[11] Patent Number: 4,510,926
[45] Date of Patent: Apr. 16, 1985

[54] SUPPORT DEVICE FOR MEDICAL INSTRUMENTS

[75] Inventor: Yutaka Inaba, Tokyo, Japan

[73] Assignee: Tokyo Medical and Dental University, Tokyo, Japan

[21] Appl. No.: 521,101

[22] Filed: Aug. 8, 1983

Related U.S. Application Data

[63] Continuation of Ser. No. 25,194, Mar. 29, 1979, abandoned.

[30] Foreign Application Priority Data

Oct. 12, 1978 [JP] Japan ................................ 53-125297

[51] Int. Cl.³ .............................................. A61B 17/02
[52] U.S. Cl. ........................................................ 128/20
[58] Field of Search .................... 128/20, 3, 10, 12, 17, 128/303 R, 303 B; 269/45, 97, 322, 328; 248/466

[56] References Cited

U.S. PATENT DOCUMENTS

| | | | |
|---|---|---|---|
| 1,524,169 | 1/1925 | Busby | 269/97 |
| 2,586,488 | 2/1952 | Smith | 128/20 |
| 2,670,732 | 3/1954 | Nelson | 128/20 |
| 3,040,739 | 6/1962 | Grieshaber | 128/20 |
| 3,046,072 | 7/1962 | Douglass et al. | 128/20 X |
| 3,129,706 | 4/1964 | Reynolds | 128/20 |
| 3,168,093 | 2/1965 | Gauthier | 128/20 |
| 4,099,521 | 7/1978 | Nestor et al. | 128/20 |
| 4,143,652 | 3/1979 | Meier et al. | 128/20 |

OTHER PUBLICATIONS

S.G & O, vol. 101, No. 1, p. 81 (Jul. 1955).
Document Re Greenberg's "Universal Retractor".
Document Re Sugita's "Cerebral Surgical Multipurpose Head Frame".
Document Re Kanshepolsky's "Brain Retractor".
Document Re Yasargil's "Flexible Arm Type Retractor".

Primary Examiner—Michael H. Thaler
Attorney, Agent, or Firm—Maky, Renner, Otto & Boisselle

[57] ABSTRACT

A support device for medical instruments such as spatulas comprises a pair of semicircular support track frames to form a circular frame on which are mounted movable bases for spatulas slidable along tracks of the semicircular support track frames, a pair of support arms each having a holder for supporting the track frames slidably thereon, detachably therefrom and clamping the track frames thereto, and support legs for supporting the support arms such that the support arms are movable upwardly and downwardly and pivotally movable relative to the support legs and rotatable about the support legs.

The support device according to the invention is capable of extending various instruments such as spatulas from a circumference toward the areas to be operated at all angles and fixing them with high accuracy and is able to change positions of the instruments with high freedom and to meet the requirements of the fine adjustment of the instruments with high accuracy. These operations of the device can be effected by an operator himself observing a spatula and deep area to be operated through an operating microscope.

9 Claims, 4 Drawing Figures

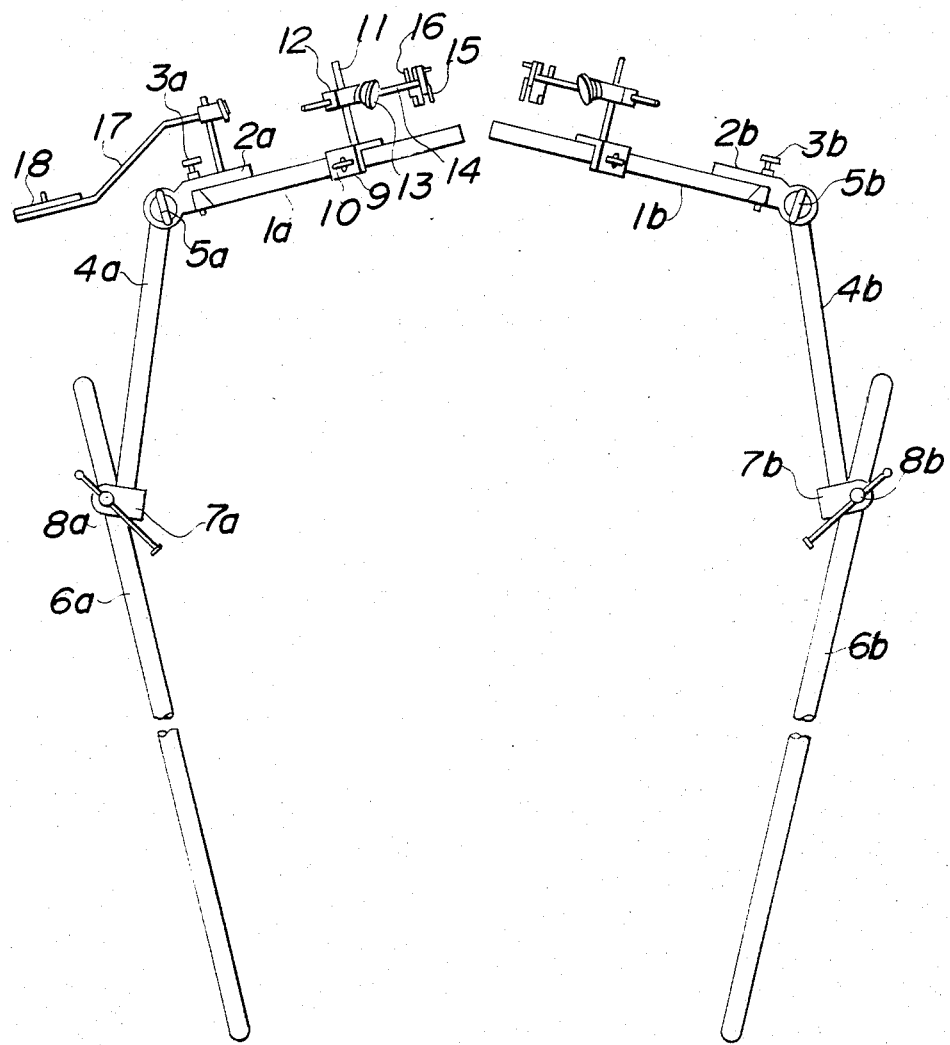
FIG_1

FIG_2
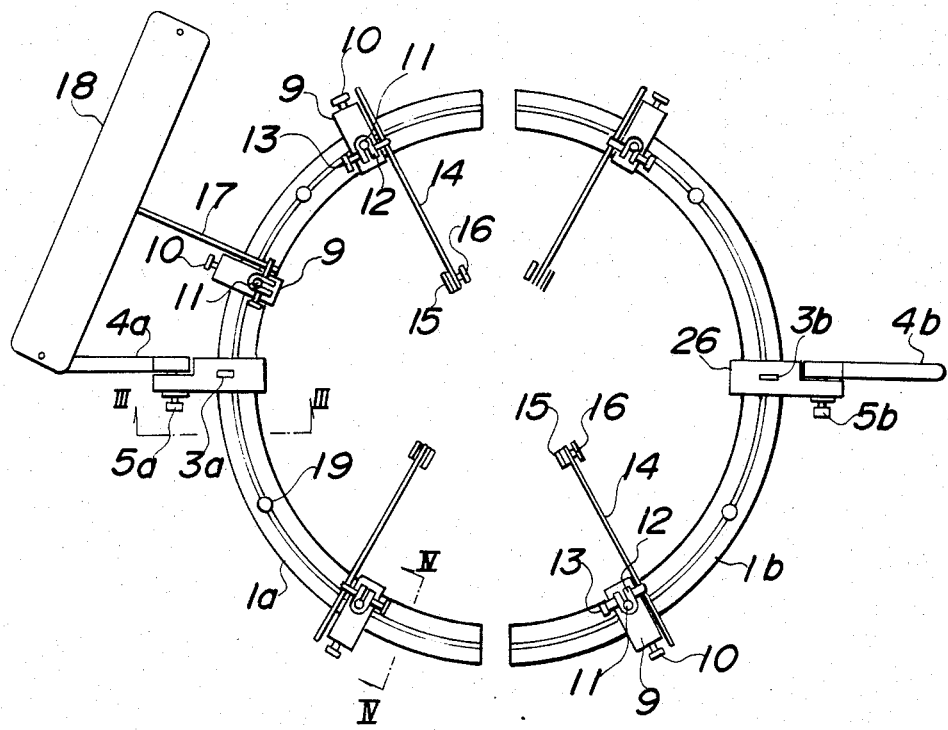

FIG_3
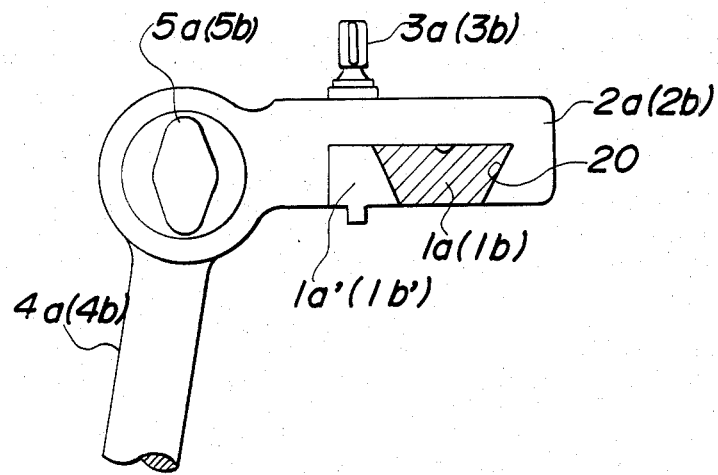
FIG_4
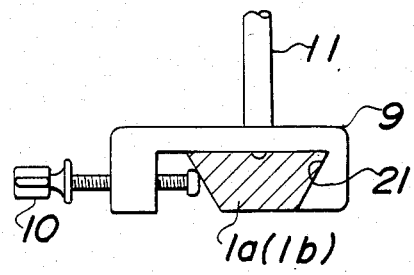

SUPPORT DEVICE FOR MEDICAL INSTRUMENTS

This application is a continuation of application Ser. No. 025,194, filed Mar. 29, 1979, now abandoned.

BACKGROUND OF THE INVENTION

1. Field of the Invention

This invention relates to a support device for medical instruments to be used for diagnosis, cure and medical treatment, and relates more particularly to support device for supporting operating instruments as spatulas and the like for cerebral microscopic operation and introducing them into fields or areas to be operated.

2. Description of the Prior Art

In cerebral surgical operation, it is generally required to reach an inner area to be operated securely, carefully displacing a brain of a patient with safety. For this purpose, spatulas have been used for long years. As the microscopic operation has become required fine operations in deeper areas, the fine adjustment and accurate holding of the spatulas in position, angle, direction and depth have been needed to a greater extent for the purpose.

The microscopic operation is generally accomplished by continuous and accumulated operations in small deep area to be operatd. In order to carry out the safe and secure operation, the path of spatula toward the target area must be narrow and as straight as possible to occupy the minimum space. The brain and structure adjacent thereto must be slightly and effectively displaced, preventing them from being wounded. Moreover the target in the deep area would be changed continuously or intermittently from a portion to another as the operation proceeds. Accordingly, various handling of the spatulas and the like for the operation must be effected with safety and security.

For this purpose, a brain protection and traction device is required to change or adjust finely its position, depth and direction and to be securely retained in position after every adjustments. In other words, the precise traction of the spatulas must be ensured in all angles, depths and positions.

The spatulas had been used being held by hand for operation and now they are often used in the same manner. However, the holding the spatula by hand is very unstable. In a fine operation in a deep area, it is quite impossible to hold a spatula unvarying without any slight movement for long hours.

In substitution for holding a spatula by hand, it has been suggested to provide a device including a rod-shaped or frame-shaped fixture onto which spatulas are fixed. However, it does not fulfil the requirements for the modern cerebral operation as follows.

The cerebral operation is not necessarily effected in a determined position and in a determined direction. It is required tomove spatulas finely and precisely and change them frequently immediately corresponding to the operations in all angles and directions. These movements of the spatulas must be effected by loosening and clamping the spatulas by hand out of the field of view of an operator by himself who is observing on the magnified tips of the spatulas and fields of the operation through an operating microscope. If the fine adjustments of the spatulas could not be freely carried out at desired time during the operation or securely holding them in the determined positions after the adjustments would not be stable, the microscopic operation will be greatly obstructed. Furthermore, the instruments and materials required for the operation must be located near the operator.

In order to fulfil these requirements, various devices have been investigated and developed, for example, Greenberg's "Universal Retractor", Sugita's "Cerebral Surgical Multipurpose Head Frame", Kanshepolsky's "Brain Retractor" and Yasargil's "Flexible Arm Type Retractor".

These devices all comprise spatula support rods which are elongated in roundabout way toward target areas to be operated. The roundabout path of the spatula support rod would obstruct the stability and accuracy in the fine positional adjustment and clamping of the spatulas. It has been found in practice that "fatigue phenomena" often occur in these device, which is a first problem to be solved.

The term "fatigue phenomenon" used herein means a phenomenon that a device exhibits an appearance as if it was senescent, resulting from increased clearances between relatively sliding parts due to wear. For example, members which should be horizontal are tilted due to increased clearance to exhibit a senescent appearance.

Although the Sugita's head frame is semicircular, it is only a single half annular frame having a narrow effective area and does not include a track for spatulas, so that the high freedom and fine adjustment could not be expected.

Greenberg's retractor includes tracks but is square configuration, so that sliding movements of spatulas are stopped at four corners to decrease the freedom and therefore roundabout rods are needed. The respective parts of the Greenberg's retractor are bulky which do not meet the fine adjustment of instruments required in the microscopic operation. This is very disadvantageous for delicate adjustments in cerebral microscopic operation.

SUMMARY OF THE INVENTION

It is therefore an object of the present invention to provide an improved support device for medical instruments such as spatulas, which eliminates the disadvantages in the prior art and which fulfils all the requirements desired for cerebral microscopic operations.

It is another object of the invention to provide a support device which is capable of extending various instruments from the circumference toward the areas to be operated at all angles and fixing them with high accuracy and which is able to change positions of the instruments with high freedom and to meet the requirements of the fine adjustment of the instruments with high accuracy and is durable in use without exhibiting the "fatigue phenomenon" and is able to be used as a rack on which are put medical materials.

The invention will be more fully understood by referring to the following detailed specification and claims taken in connection with the appended drawings.

BRIEF DESCRIPTION OF THE DRAWINGS

FIG. 1 is a front elevation of one embodiment of the support device for medical instruments according to the invention;

FIG. 2 is a plan view of a pair of support track frame of the support device shown in FIG. 1;

FIG. 3 is a sectional view taken along a line III—III in FIG. 2; and

FIG. 4 is a sectional view taken along a line IV—IV in FIG. 2.

DETAILED DESCRIPTION OF THE PREFERRED EMBODIMENTS

Referring to FIGS. 1 and 2 which illustrate a preferable embodiment of the present invention, a support device comprises a pair of semicircular support track frames 1a and 1b to form an annular frame (FIG. 2). The pair of semicircular support track frames 1a and 1b are supported in symmetry or angularly oppositely at an any angle by means of support arm mechanisms described later which are articulately and pivotally moved themselves. The support track frame 1a or 1b has an inverted trapezoidal crosssection as shown in FIG. 3 and is slidably fitted in a dovetail groove 20 of a holder 2a or 2b with the aid of a gib 1a' 1b' and clamped in position to the holder by means of a knob 3a or 3b for locking.

The holder 2a or 2b is pivotally or articulately movably connected to a support arm 4a or 4b and is adapted to be clamped thereto by means of a knob 5a or 5b for locking. The support arm 4a or 4b is connected to a support leg 6a or 6b by means of a connector 7a or 7b in a manner such that the support arm is raised and lowered relatively to the support leg and is articulately or pivotally movable relative to and rotatable around the support leg. In other words, the support arm is movable relative to the support leg in the four kinds of the movements. The connector 7a or 7b integral with the support arm permits such four kinds of the movements of the support arm relative to the support leg and is clamped thereto in position by means of a locking rod 8a or 8b.

The support legs 6a and 6b are directly or indirectly supported on an operating table (not shown). The support legs 6a and 6b may be supported on the table adjustably in angle to a horizontal.

On the semicircular support track frames 1a and 1b are positionally adjustably arranged support members for spatulas (not shown) and other instruments. For this purpose, on the support track frames 1a and 1b are slidably fitted movable bases 9 each formed with a dovetail groove 21 and a column 11 uprightly standing on its upper surface and provided with a lock screw rod 10 abutting against the support track frame 1a or 1b.

On the column 11 of each the movable base 9 is mounted a spatula support 14 and other instrument. In the shown embodiment, the spatula supports 14, 15 and 16 are supported on the base 9 through a connector member 12 supported in a direction crossing column 11 in a manner such that the support rod 14 is movable upwardly and downwardly and is pivotally movable relative to and rotated about the column 11. The support rod 14 is clamped in position to the column 11 by means of a lock knob 13 by a single operation. Spatula gripping jaws 15 are adjustably secured to the distal end of the support rod 14 and are adapted to be clamped in position to the support rod 14 by a lock knob 16.

A plurality of such spatula supports 14, 15 and 16 whose number is selected according to the required condition are arranged on the semicircular support track frames 1a and 1b at any interval and radially toward the center of the circle of the support track frame. Any instruments other than the spatulas may be arranged on the columns 11 of the movable bases 9. For example, a T-shaped support rod 17 is adjustably mounted on the connector member 12 radially outwardly of the track frame in the same manner as the support rod 14 and is detachably provided on its outer end with a rectangular base plate 18 for putting medical supplies such as absorbent cotton for an operation. The rectangular base plate may of course be arranged on the other support track frame 1b. The support track frames 1a and 1b may be formed in suitable positions with threaded apertures 19 for enabling other instruments to be mounted. An illuminator (not shown) may be mounted on the support track frame by means of the holder or by the use of the threaded aperture.

In using the support device according to the invention, the two semicircular track frames 1a and 1b are located in symmetry or oppositely at any angle to meet the spherical surface of a cranium of a patient to be operated. For this purpose, the support legs 6a and 6b are fixed to rails arranged on an operating table and onto the support legs 6a and 6b are fixed support arms 4a and 4b to which are connected the holders 2a and 2b and the support track frames 1a and 1b such that crossing angles and relative positions of these adjacent members can be freely selected.

On the tracks of the support track frames 1a and 1b are fitted any plurality (maximum ten) of the movable bases 9 on which are mounted the spatula supports 14, 15 and 16. The spatulas are fixed to the spatula supports so as to extend therefrom in desired lengths at required angles. During an operation the movable bases 9 are slid at any time and the spatula supports are moved to change the positions, angles and lengths of the spatula supports if desired and thereafter clamped at any positions. The column 11 of the movable bases 9 may be provided with the T-shaped support rod 17 having at its end the base plate 18. The column may be provided with a supplementary illuminator, a suction nozzle, a water supply tube and the like supported by respective support columns and may be movable at any time as the case may be.

With this above function and arrangement the support device according to the invention is capable of positioning the pair of semicircular support track frames to meet all the positions of heads or skulls of patients to be operated and clamping the support track frames in the most suitable positions and angles to carry out the operation. Fixed annular frames of the prior art could not obtain such a universal adaptability of the invention and is much inferior in performance to the invention. The device according to the present invention comprises the semicircular frames to form a complete circle, so that the operative area or direction, to which the spatulas can be applied effectively, is about twice greater than that of a single semicircular frame as in the "Cerebral Surgical Multipurpose Head Frame" in the prior art and the forces such as traction forces can be effectively applied from all the outer positions radially inwardly toward a target or areas to be operated.

The support device according to the present invention comprises the support frames including the tracks, which is much higher in freedom for positioning instruments slidable along the tracks than that in the prior art where instruments are fixed in limited ranges, and which always rapidly fulfils the requirement of the fine changes in position of the instruments with high accuracies. The device according to the present invention can always hold the instruments on the annular (substantially completely circular) tracks with the shortest distances to the inner target in the zone to be operated at the center of the circle, so that the maximum stability of the instruments can be obtained with the minimum physical forces.

With this effective utilization of the forces, the device according to the invention can eliminate the fatigue phenomenon of devices which would often occur in the prior art. In the prior art, required forces are unavoidably applied to a target through roundabout ways, so that the holding of the instruments becomes very unstable in finely adjusting them, resulting in lower accuracy in fixing them at desired positions and the fatigue of the device could not be avoided. As the result, it is very difficult to fix an instrument as a spatula with high accuracy after a fine adjustment required in a microscopic operation, because of the roundabout forces in the prior art. The present invention has solved this problem. Furthermore, the device according to the invention includes the smooth tracks on which the instruments can be finely adjusted and slidable with ease. The support device according to the invention achieves the fine adjustment and precise fixation of the instruments which are absolutely required in the microscopic operation of deep portions in the brain.

In the fine adjustment and fixation of the instruments, according to the invention an operator can easily handle and clamp the movable bases 9, support rods 14 and connector members 12 on the tracks, observing a spatula and deep areas to be operated through a microscope. The fine changes in positions of these members required for the operation can be carried out safely and surely to all angular positons in all directions with respect to the areas to be operated.

Furthermore, the support device according to the invention has an advantage in that a number of multipurpose instruments other than the spatula are mounted on the movable bases, which could not obtain in the prior art. The remarkable usefulness of the device according to the invention has been proved in more than 150 cases of the cerebral microscopic operations which were carried out by the use of the device according to the invention by the inventor of this application. It is clearly evident that the present invention has remarkably improved the contents of operations in comparison with the prior art. On the other hand, the superiority of the present invention has also been proved by the fact that there was no case of operation with an unfavorable result.

While the invention has been particularly shown and described with reference to preferred embodiment thereof, it will be understood by those skilled in the art that the foregoing and other changes in form and details can be made therein without departing from the spirit and scope of this invention.

What is claimed is:

1. A support device for medical instruments comprising a pair of independently adjustable semicircular support track frames that can be positioned in different planes and at different angles with respect to each other to optimize the direction in which operating elements such as spatulas can be applied, a support arm for each frame, each support arm having a holder for supporting its respective track frame slidably thereon and detachably therefrom and clamping the track frame thereto, and support legs for respectively supporting said support arms, said support arms being movable upwardly and downwardly and pivotally movable relative to the support legs and rotatable about the support legs by means of connectors, and each holder being pivotally movably connected to the respective support arm and clamped thereto by clamping means.

2. A support device as set forth in claim 1, wherein on said support track frames is provided at least one movable base slidable along a track of the support track frame, fixable in any position and detachable therefrom.

3. A support device as set forth in claim 2, wherein said movable base is provided with a column uprightly standing thereon, on which column is mounted a spatula support in a manner such that it is movable upwardly and downwardly and pivotally movable relative to said column and rotatable about said column and fixable in a desired position, and other said movble base is provided with a column for other medical instrument.

4. A support device as set forth in claim 1, wherein each said semicircular support track frame is formed with a semicircular track along which movable bases for medical instruments are slidable.

5. A support device as set forth in claim 1, wherein said support arm is connected to the support leg by means of a connector which is integrally formed with said support arm and is clamped to said support leg by means of a locking rod.

6. A support device for medical instruments comprising a pair of semicircular track frames positionable to form a generally circular frame, and respective means for independently adjustably supporting said track frames for substantial universal orientation with respect to one another, each means for supporting including a holder for slidably supporting the respective track frame, means for clamping the track frame to said holder, a support arm for said holder, a support leg for said support arm, and releasable clamp means for adjustably securing said support arm to said support leg, said clamp means when released allowing upward and downward movement, pivotal movement and rotatable movement of the support arm relative to the support leg, and said holder of each means for supporting being pivotally connected to the respective support arm for pivotal adjustment and clamped thereto by a releasable clamping device.

7. A support device as set forth in claim 5, wherein each means for supporting includes an articulated three linkage assembly.

8. A support device for medical instruments comprising a pair of independently adjustable semicircular support track frames that can be positioned in different planes and at different angles with respect to each other to optimize the direction in which operating elements such as spatulas can be applied, a support arm for each frame, each support arm having a holder for supporting its respective track frame slidably thereon and detachably therefrom and clamping the track frame thereto, and support legs for respectively supporting said support arms, said support arms being movable upwardly and downwardly and pivotally movable relative to the support legs and rotatable about the support legs by means of connectors, and each said semicircular support track having an inverted trapezoidal cross section and being slidably fitted in a dovetail groove of said holder with the aid of a gib and clamped to said holder by means of clamping means.

9. A support device for medical instruments comprising a pair of semicircular track frames positionable to form a generally circular frame, and respective means for independently adjustably supporting said track frames for substantial universal orientation with respect to one another, each track frame having a trapezoidal cross-section, and each means for supporting including a holder having a dovetail groove in which the respective track frame is slidably fitted, and means for clamping the track frame to the holder with the aid of a gib.

* * * * *